(12) United States Patent
Yockney

(10) Patent No.: US 8,300,502 B2
(45) Date of Patent: Oct. 30, 2012

(54) METHOD AND SYSTEM FOR ACOUSTIC IMAGING USING A PLURALITY OF TRANSMITTING ARRAYS ON A CIRCUMFERENTIAL SURFACE

(75) Inventor: Rob K. Yockney, Templecombe (GB)

(73) Assignee: Thales Holdings UK PLC, NR Weybridge, Addlestone Surrey (GB)

( * ) Notice: Subject to any disclaimer, the term of this patent is extended or adjusted under 35 U.S.C. 154(b) by 274 days.

(21) Appl. No.: 12/419,506

(22) Filed: Apr. 7, 2009

(65) Prior Publication Data
US 2009/0274006 A1 Nov. 5, 2009

(30) Foreign Application Priority Data
Apr. 7, 2008 (GB) .................................. 0806292.9

(51) Int. Cl.
*H04B 1/02* (2006.01)
(52) U.S. Cl. .......................................... 367/138; 73/625
(58) Field of Classification Search .................... 367/11, 367/138, 88, 119; 73/625
See application file for complete search history.

(56) References Cited

U.S. PATENT DOCUMENTS

| | | | |
|---|---|---|---|
| 4,209,856 A | 6/1980 | Henning et al. | |
| 4,227,417 A | 10/1980 | Glenn | |
| 5,287,330 A * | 2/1994 | Gilmour | 367/103 |
| 5,511,043 A * | 4/1996 | Lindberg | 367/155 |
| 5,535,751 A * | 7/1996 | Raz | 600/459 |
| 5,787,049 A * | 7/1998 | Bates | 367/7 |
| 5,839,442 A * | 11/1998 | Chiang et al. | 600/447 |

(Continued)

FOREIGN PATENT DOCUMENTS
EP 1348954 A1 10/2003
(Continued)

OTHER PUBLICATIONS

Dhanantwari, A.C.; Stergiopoulos, S.; Song, L.; Parodi, C.; Bertora, F.; Pellegretti, P.; Questa, A.; , "An efficient 3D beamformer implementation for real-time 4D ultrasound systems deploying planar array probes," Ultrasonics Symposium, 2004 IEEE , vol. 2, No., pp. 1421-1424 vol. 2, Aug. 23-27, 2004.*

(Continued)

*Primary Examiner* — Isam Alsomiri
*Assistant Examiner* — James Hulka
(74) *Attorney, Agent, or Firm* — Stroock & Stroock & Lavan LLP

(57) ABSTRACT

The invention relates to an imaging method and system for providing acoustic images of a surface and more particularly, but not exclusively, to acoustic imaging of a surface within a confined space. Also described are an acoustic probe and a transmit/receive sensor array configuration to implement the imaging method and system. The probe has an array of acoustic transmitters arranged in juxtaposed or spaced relationship around at least a portion of the circumferential surface of the probe, and an array of acoustic receivers also disposed around at least a portion of its circumferential surface. A beamformer is used for focussing and steering the acoustic beams from the acoustic transmitter array onto portions of the structure to be examined and for focussing and steering the receive beams onto said surface portions, said beam-former adapted to cause the acoustic transmit beams to be focussed in a plane orthogonal to the plane used to focus the receive beams. High resolution in the near field can be achieved by focussing the transmit and receive beams onto a surface at a focus region, the focus region being narrow in both the orthogonal planes.

18 Claims, 5 Drawing Sheets

U.S. PATENT DOCUMENTS

| | | | |
|---|---|---|---|
| 5,923,617 A * | 7/1999 | Thompson et al. | 367/103 |
| 6,076,407 A * | 6/2000 | Levesque et al. | 73/623 |
| 6,111,816 A * | 8/2000 | Chiang et al. | 367/7 |
| 2001/0017541 A1 * | 8/2001 | Kwun et al. | 324/240 |
| 2002/0012289 A1 * | 1/2002 | Gilbert et al. | 367/135 |
| 2002/0064093 A1 * | 5/2002 | Chiang et al. | 367/138 |
| 2002/0071345 A1 * | 6/2002 | Chiang et al. | 367/138 |
| 2002/0080683 A1 * | 6/2002 | Chiang et al. | 367/138 |
| 2003/0214880 A1 * | 11/2003 | Rowe | 367/103 |
| 2003/0231547 A1 * | 12/2003 | Yang | 367/11 |
| 2004/0050167 A1 * | 3/2004 | Linares et al. | 73/622 |
| 2004/0069069 A1 * | 4/2004 | Gysling et al. | 73/736 |
| 2004/0208084 A1 * | 10/2004 | Guthmann | 367/88 |
| 2004/0211261 A1 * | 10/2004 | Prause | 73/644 |
| 2005/0007882 A1 * | 1/2005 | Bachelor et al. | 367/103 |
| 2005/0113694 A1 * | 5/2005 | Haugen et al. | 600/443 |
| 2005/0113699 A1 * | 5/2005 | Haugen et al. | 600/459 |
| 2008/0130413 A1 * | 6/2008 | Bachelor et al. | 367/103 |

FOREIGN PATENT DOCUMENTS

| | | |
|---|---|---|
| GB | 2192715 | 1/1988 |

OTHER PUBLICATIONS

Kirkebo, Jan Egil; Austeng, Andreas; "Improved beamforming using curved sparse 2D arrays in ultrasound", Ultrasonics, vol. 46, Issue 2, May 2007, pp. 119-128.*

* cited by examiner

METHOD AND SYSTEM FOR ACOUSTIC IMAGING USING A PLURALITY OF TRANSMITTING ARRAYS ON A CIRCUMFERENTIAL SURFACE

CROSS-REFERENCE TO RELATED APPLICATIONS

The present application claims the benefit of British Patent Application No. 08 06292.9, filed Apr. 7, 2008 which is hereby incorporated by reference in its entirety.

BACKGROUND OF THE INVENTION

1. Field of the Invention

The present invention relates generally to an imaging method and system for providing acoustic images of a surface or boundary and more particularly, but not exclusively, to acoustic imaging of a surface or boundary within a confined space. Also provided is an acoustic probe and a transmit/receive sensor array configuration for implementing the imaging method and system.

2. Description of the Related Art

There are many applications in which the image of a surface requires inspection within a confined space. For example, in the field of oil extraction, an oil extraction pipe is housed concentrically within a larger diameter steel pipe, which acts as a casing for isolating the well bore and the extraction pipe, from potentially dangerous high-pressure zones. The steel casing pipe is cemented in place within the well bore and has a diameter of between 5 to 30 inches (13-76 cm), the range of size accommodating different diameters of well bore which may decrease in several stages as the well bore passes deeper below the surface. The oil extraction pipe typically has a diameter of 4 inches (10.16 cm).

It is necessary to check the integrity of the oil extraction pipe structure by inspecting the inner surface of the pipe to investigate fractures, damage or other effects, such as the build up of sediment, which may hinder or prevent the extraction of oil along the pipe. As the pipe is only 4 inches in diameter the devices adopted to carry out the inspection are restricted in size. Furthermore, other technical constraints are encountered related to the application. For example, if an optical probe, such as endoscope or a camera, is employed as the detector the pipe must be flushed out of oil in order that optical images of the internal surface of the pipe can be obtained. This requirement is time consuming and results in an interruption in oil extraction, which is both inconvenient and expensive. Damage in the extraction pipe often occur at about sea level but they can also occur below. If long lengths or the whole of the extraction pipe are to be inspected, which may pass several kilometers or more beneath the surface, the cost of an internal inspection may become prohibitively expensive.

It is desirable to find a method in which the inside surface wall of the pipe can be examined without the need to flush the oil from the pipe first.

One advantage of a sonar probe is its ability to derive an image of an object or surface irrespective of whether or not the medium between the probe array sensors and the object or surface under inspection is transparent to light. An appropriate sound speed can be used in the calculation of the waveform generation and processing to compensate for the different speed of sound of different medium. However, using known sonar probes for this purpose give rise to technical difficulties associated with adequate image resolution, these difficulties arising primarily because of the "near-field" imaging effects encountered in confined spaces.

At short distances from a transmit array, the individual parts of the array have significantly different path lengths and as a consequence create an irregular pattern of intensity. This region is known as the 'near' field. As the range is increased the differences in the path length across the array gradually reduce to the point where they eventually become insignificant and the energy is considered to emanate from a point source. This region is referred to as the 'far' field.

For a receive array a similar effect occurs whereby echoes from objects in the far field can be considered to produce planar wave fronts whereas those from objects in the near field are significantly spherical.

In both cases the transition range between the 'near' and 'far' fields is determined from the array aperture and the acoustic wavelength at the operating frequency in the propagation medium as follows:

$$\text{Transition range} = \{(\text{Length of acoustic aperture})^2 \times \pi\} / \{4 \times \text{wavelength}\}$$

The array aperture is typically the length of the array, and if the array has a curvature the array aperture can be construed as the length of a straight line between and joining the ends of the array.

BRIEF SUMMARY OF THE INVENTION

The present invention strives to provide a method and system of acoustic imaging providing an acceptable image resolution in confined spaces.

According to one aspect of the invention there is provided an acoustic imaging system for imaging a structure or boundary, the system comprising a probe having an array of acoustic transmitters arranged in juxtaposed or spaced relationship around at least a portion of the circumferential surface of the probe, and an array of acoustic receivers disposed around at least a portion of the circumferential surface the probe, beam forming means for focussing and steering the acoustic beams from the acoustic transmitter onto portions of the structure or boundary to be examined and for focussing and steering the receive beams onto said surface or boundary portions, said beam forming means adapted to cause the acoustic transmit beams to be focussed in a plane orthogonal to the plane used to focus the receive beams.

In one embodiment the region of focus of the transmit beam has a longer (or wider) dimension in the plane extending radially outward from the probe compared to the region of focus of a receive beam, and in the orthogonal plane thereto, the region of focus of the transmit beam has a shorter (or narrower) dimension compared with the region of focus of the receive beam.

In an alternative embodiment the region of focus of the transmit beam has a shorter (or narrower) dimension in the plane extending radially outward from the probe compared to the region of focus of a receive beam, and in the orthogonal plane thereto, the region of focus of the transmit beam has a longer (or wider) dimension compared with the region of focus of the receive beam.

In a further alternative embodiment the region of the focus of the transmit beam has longer (or wider) dimensions compared to the region of focus of a receive beams in both the plane extending radially outward from the probe and the orthogonal plane thereto.

The imaging system can be provided with steering and focussing means to focus transmit and receive beams onto a surface or boundary at a focus region, the focus region being narrow in both the orthogonal planes.

In one embodiment the transmitter and receiver arrays are disposed about a common axis, for example the probe may be cylindrical with the arrays sharing the common central axis through the cylindrical configuration. The arrays may be formed as rings extending around the outer surface of the probe thereby enabling the probe to be inserted into a pipe or tube to scan the inner surface without angular relative rotation between the probe and pipe or tube. The arrays and surface under inspection are concentric.

The transmitter array can be formed as a plurality of transmitter rings, each transmitter ring comprising one transmitter element. Alternatively each transmitter ring may comprise a plurality of transmitter elements.

Each transmitter element is typically associated with a respective amplifier and therefore to keep the complexity of the electronics as simple as possible it is convenient for each transmitter ring to consist of just one transmitter element.

In contrast the receiver array may be just a single ring comprising a plurality of separate receiver elements, for example 256 receiver elements.

The system controlling the arrays enables them to be focussed dynamically. This is a desirable feature as in operation during an inspection process, with the probe disposed within for example a pipe, an approximate, predetermined range can be used initially for focussing the receive beams onto the receiver array. However, each beam has a depth of focus, so it will image on either side of the focal point of the beam providing poorer images the greater the distance away from the focal point. The focussing of the receive beams can thus be dynamically adjusted to ensure the focal point of the beam is focussed on the surface under examination.

In various embodiments of the invention the receiver array can be located on either one or both sides of the transmitter array and/or disposed in a central region of the transmitter array.

In an alternative embodiment, the array of acoustic transmitters may be arranged in juxtaposed or spaced arcs on the probe surface, and the array of acoustic receivers may be disposed likewise as an arc on the probe surface. Typically, the arcs may subtend 60, 90 or 180 degrees, enabling a full scan of an inner concentric surface to be established by relative angular rotation in steps of 60, 90 or 180 degrees between the probe and concentric surface under inspection.

The probe may be non-cylindrical, for example the acoustic transmitters and receivers may be formed around the surface of a probe having a square or other polygonal cross-section. In such an embodiment the arrays may also be formed either completely around the circumferential surface or on just portions thereof, for example located on one or two of the side surfaces defining the polygonal shape.

In one embodiment of the invention the probe utilises a cylindrical Mill's Cross transmit/receive transducer arrangement to produce transmit acoustic beams that are omni-directional in the radial plane of the cylinder and narrow in the orthogonal plane. High resolution images are created inside the system's 'near fields' of both planes by arranging for the transmit beams to be focussed in a plane orthogonal to the plane used to focus the receive beams whilst the probe is moved parallel to the surface being imaged.

In a further aspect of the invention there is provided a method of sonar imaging an area under investigation, comprising transmitting beams from an array of acoustic transmitters arranged in juxtaposed or spaced relationship around at least a portion of the circumferential surface of a probe, receiving reflected beams from the area under investigation which are sensed by acoustic receivers disposed around at least a portion of the circumferential surface of the probe to produce a plurality of output signals from said acoustic receiver sensors, and processing said output signals to provide an image of the area under investigation, wherein the transmitter beams are focussed and steered from the transmitter array onto portions of the area to be examined in a plane orthogonal to the plane used to focus and steer the receive beams.

In one embodiment the method comprises mounting the transmitter and receive arrays on the surface of a probe and driving the transmitter array and processing the receive array signals so that the region of focus of the transmit beam has a longer (or wider) dimension in a plane extending radially outward from the probe compared to the region of focus of a receive beam, and in the orthogonal plane thereto, the region of focus of the transmit beam having a shorter (or narrower) dimension compared with the region of focus to the receive beam.

In an alternative embodiment the method comprises mounting the transmitter and receive arrays on the surface of a probe and driving the transmitter array and processing the receive array signals so that the region of focus of the transmit beam has a shorter (or narrower) dimension in a plane extending radially outward from the probe compared to the region of focus of a receive beam, and in the orthogonal plane thereto, the region of focus of the transmit beam having a longer (or wider) dimension compared with the region of focus of the receive beam.

In a further alternative embodiment the method comprises mounting the transmitter and receive arrays on the surface of a probe and driving the transmitter array and processing the receive array signals so that the region of the focus of the transmit beam has longer (or wider) dimensions compared to the region of focus of a receive beams in both the plane extending radially outward from the probe and the orthogonal plane thereto.

The method may comprise the step of dynamically controlling the focal point of the beam associated with one or both of the arrays.

A large number of receive beams can be then produced that are narrow in the plane of the probe, for example, and wide in the orthogonal plane or vice versa. By steering and focussing transmit and receive beams onto a surface or boundary at a focus region, the focus region can be narrow in both of the orthogonal planes.

In one embodiment of the method, the narrow transmit beam is focussed at a user defined range whilst the receive beams are automatically focussed dependent on the range. The short range enables a fast ping rate thus enabling the user to dynamically focus the image by controlling the focus range of the transmit beam.

In a further aspect of the invention there is provided an acoustic array configuration comprising an array of acoustic transmitters arranged in juxtaposed or spaced relationship around at least a portion to the circumferential surface of a probe, for transmitting sonar signals to an area under investigation and an array of acoustic receivers disposed around at least a portion of the circumferential surface of the probe for receiving reflected acoustic signals, said array of acoustic transmitters being located relative to the acoustic receivers in a disposition whereby transmitter beams can be focussed from the transmitter array onto portions of the area to be examined in a plane orthogonal to the plane used to focus and steer the received reflected beams.

In a further aspect of the invention there is provided a probe comprising the sonar array configuration defined above.

In a yet further aspect of the invention there is provided a method of inspecting the inside surface of a pipe containing a fluid comprising inserting into the pipe a probe carrying a sonar array configuration having a transmitter array and a receiver array, transmitting beams from the transmitter array through the fluid to an area of the surface to be imaged, receiving reflected signals from the area under investigation which are sensed by acoustic receiver sensors in a receiver array to produce a plurality of output signals from said acoustic receiver sensors, and processing said output signals to provide an image of the area under investigation, wherein the transmitter beams are focussed from the transmitter array onto portions of the area to be examined in a plane orthogonal to the plane used to focus the receive beams.

In one embodiment of the method the pipe is an oil extraction pipe and the fluid is oil.

In a further aspect of the invention there is provided a computer program product operable, when executed on a computer, to cause said computer to perform the method according to the invention. Furthermore there is provided a computer readable storage device storing a computer program product, the computer readable storage device being, for example, a magnetic or optical disk, or a memory device, or a hardware implementation such as an ASIC. Also provided is a computer receivable signal carrying a computer program product according to the invention.

BRIEF DESCRIPTION OF THE DRAWINGS

The present invention will be described further, by way of example, with reference to the accompanying drawings in which.

DETAILED DESCRIPTION

In the following description, specific implementations of the invention are described. It will be appreciated by the reader that these are provided by way of example only, and are not intended to provide restriction or limitation on the scope of the invention which is defined in the appended claims.

Figure 1:
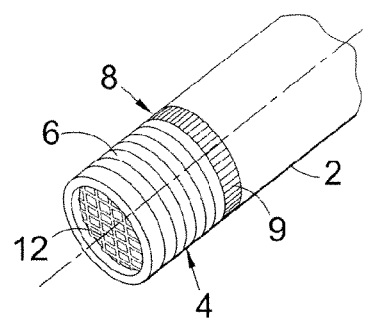
FIG. 1 illustrates an acoustic sensor in accordance with one embodiment of the present invention.

FIG. 1 illustrates an acoustic sensor in accordance with one embodiment of the present invention. The sensor is in the form of a cylindrical probe 2 and is provided at one end with a transmitter array 4 comprising a plurality of spaced transmitter rings 6, each transmitter ring 6 being in the form of one or more transmitter elements. Each of the transmitter elements is connected to a respective amplifier not shown in FIG. 1 for the sake of simplicity. The example shown in FIG. 1 contains 6 transmitter rings. In practice there can be 3 or more. Also provided on the probe 2 is a receiver array 8 defined by a single ring of 256 receiver elements 9. Each of the receiver elements 9 is also connected to a respective amplifier not shown. In practice more than one receiver ring can be used however this will increase the electronic complexity of the system.

The transmitter array 4 and the receiver array 8 are concentrically disposed around a central axis 12 of the cylindrical probe 2, the receiver array 8 being disposed at the same radial distance from the axis 12 as the transmitter array 4. Whereas it is desirable to have both the transmitter and receiver arrays 4, 8 disposed at the same radial distance from the axis 8, it is not essential as their focussing is achieved independently. In FIG. 1, for example, the transmitter array 4 is provided on a reduced diameter at the end of the cylinder.

Figure 11:
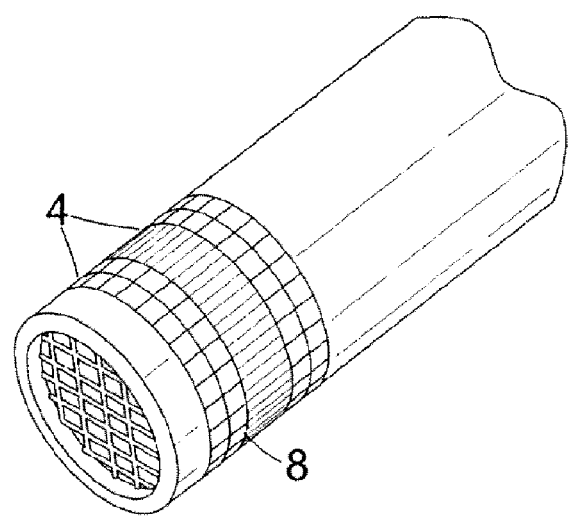
FIG. 11 illustrates a further embodiment of the acoustic sensor configuration with the receive array positioned within transmit array.

In other embodiments the receiver array 8 can be disposed on the other side of the transmitter array 4 at the end of the cylindrical probe 2, or can consist of two spaced rings, one on each side of the transmitter array 4. Alternatively or in addition a ring of receiver elements can be located within a region of the transmitter array 4. FIG. 11 illustrates an embodiment in which the receiver array 8 is located in the centre of the transmitter array 4, however it is not necessary for the receiver array 8 to be at the centre of the transmitter array 4. The receiver and transmitter arrays 8, 4 have been shown located at the end region of the cylindrical probe 2 in FIG. 1, however they can be located at any desired position along the length of the probe 2.

Referring to FIG. 1 it can be seen that the probe 2 is utilising a cylindrical Mill's Cross transmit/receive transducer arrangement to produce transmit/receive acoustic beams. Each of the rings 6 of the transmitter array 4 is shown orthogonally disposed on the probe 2 relative the transducer elements 9 that make up the receiver array 8.

Figure 2:
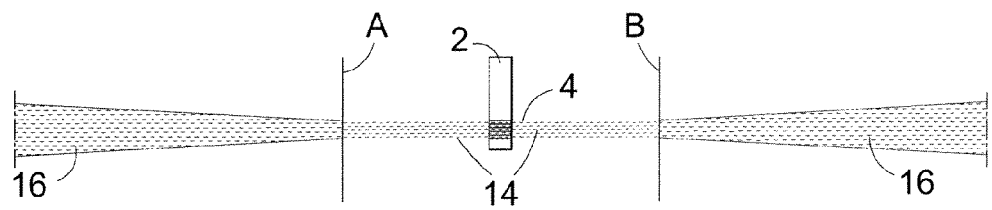
FIG. 2 is a schematic illustration showing beams focussed from the sensor of FIG. 1 propagating in the near field and in far field.

The manner in which the transmit beam is focussed is illustrated in FIGS. 2, 3, 4 and 5. A separate, respective amplifier (not shown) drives each of the rings 6 of the transmitter array 4. Referring to FIG. 2, when the amplifiers are driven by the same signal the transmitter array 4 naturally forms an omni-directional transmitted beam 14 propagating radially from the transmitter array 4. The transmitted beam 14 will not be fully divergent until in the far field, shown in FIG. 2 as beam 16, when the beamwidth is a function of the frequency of the drive signal and the aperture formed by the rings 6. The boundary between the near field and the far field is represented in FIG. 2 by the vertical lines A and B. The boundary when viewed in three dimensions is cylindrical and surrounds a portion of the probe 2 at a radial distance from the transmitter 4.

Figure 3:
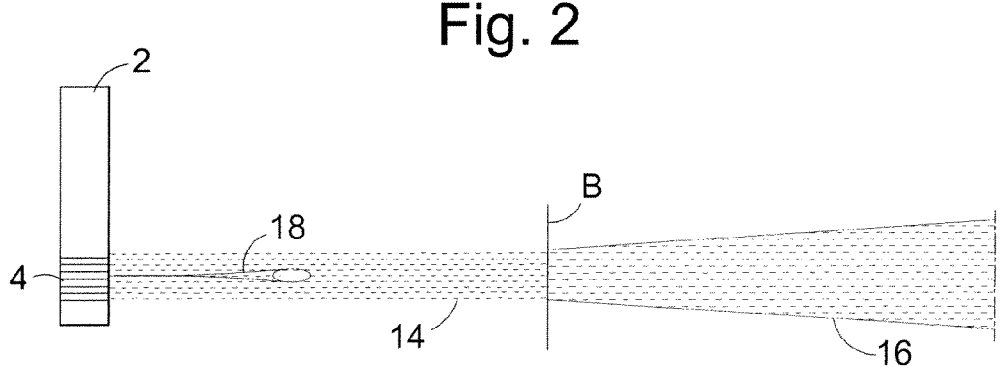
FIG. 3 is an enlarged detail from part of FIG. 2.

By time delaying the drive to the rings 6 it is possible to steer the beam relative to the plane of the rings 6 and to focus the beam such that it forms at short range a similar angular relationship to the far field beam. The focussed beam is shown in FIG. 3 as beam 18.

Figure 4:
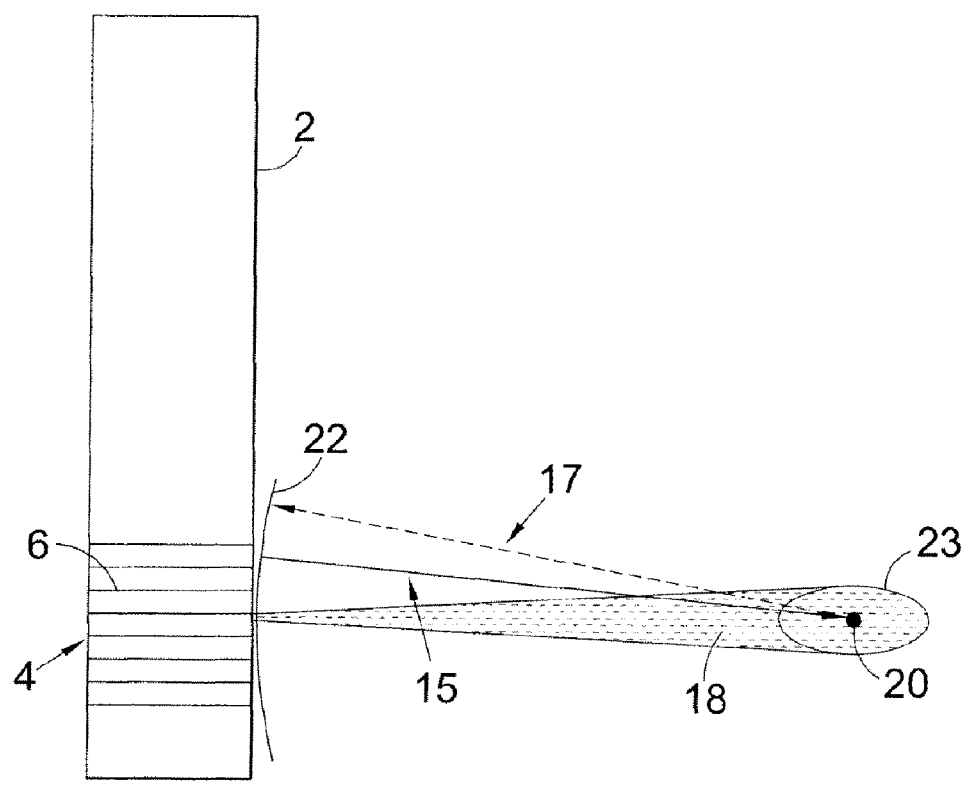
FIG. 4 is an enlarged detail from part of FIG. 3.

A more detailed illustration of the method by which the beam 18 is focussed can be seen with reference to FIG. 4. By choosing the time delays for driving each ring 6 to create a curved wave front 22 in front of the array 4, the beam 18 is focussed around a defined focus region 23 close to the array 4 and well inside the far field. The time differences in the signals used to drive the rings 6 of the transmitter array 4 are determined by the time taken for an acoustic signal to propagate to a desired wave front 22 along a straight-line path 15 from each ring 6 to a common focal point 20. The signals driving the inner rings are delayed compared to those of the outer rings such that the acoustic signals from all rings arrive at the wavefront 22 simultaneously. The radius of the concave wave front 22 is illustrated in FIG. 4 by the line 17.

Figure 5:
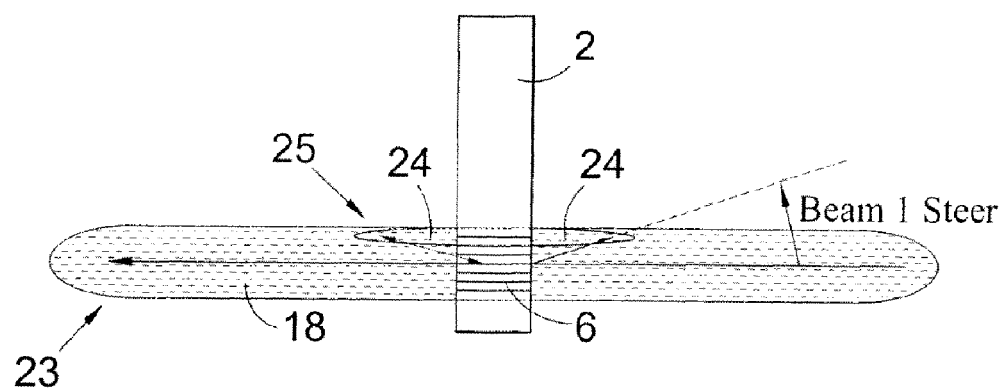
FIG. 5 shows two examples, one of a focussed beam and the other of a beam that has been both steered and focussed from the sensor of FIG. 1.

Furthermore by time delaying the drive signals to the individual rings 6, beams can be formed that are both steered and focussed at short range. Being formed by ring arrays, the locus of the focal points of the beam will create circles around the array that are at the same radius and steer angle. FIG. 5 illustrates two examples, the focussed beam 18 and a beam 24 that has been both steered and focussed, the steering angle being shown as θ.

Figure 6:
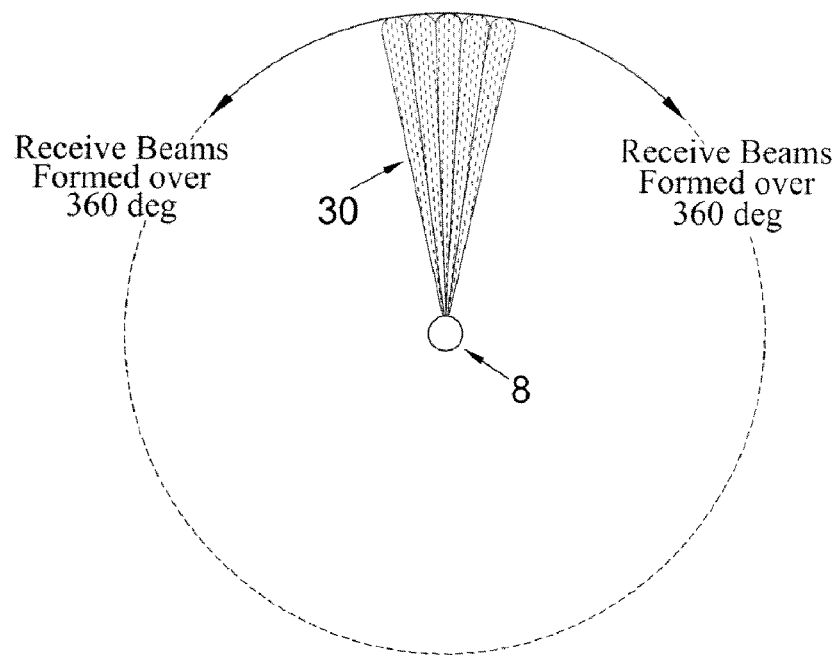
FIG. 6 illustrates how a section of the receiver ring array shown in FIG. 1 is driven to form narrow beams spreading radially outward from the ring array.

The receiver array 8 comprises a single ring of hydrophone elements, with sections of the ring being used to form narrow beams radially spreading from the ring. This process is shown in FIG. 6 in which the receive beams 30 are formed over 360 degrees.

Figure 7:
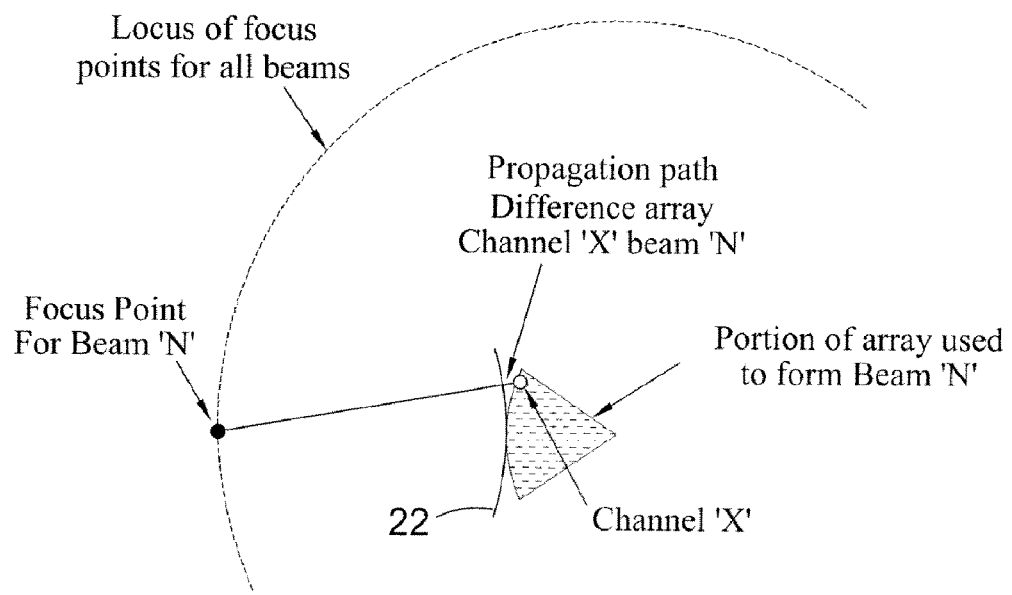
FIG. 7 illustrates how by time delaying the received signals by delays that cancel out the propagation time for the path lengths, to the different receiver elements used to form the beam, the beams can be focussed at short range.
Figure 8:
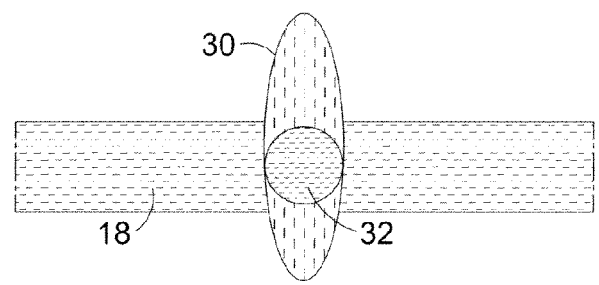
FIG. 8 is an illustration showing how it is possible by employing the sensor of FIG. 1 to focus the transmit and receive beams onto a surface at a focus range that is narrow in both planes.

By time delaying the received signals by delays that cancel out the differences in propagation time for the path lengths, to the different elements used to form the beam, the beams are focussed at short range by the wavefront 22, as shown in FIG. 7.

Figure 9:
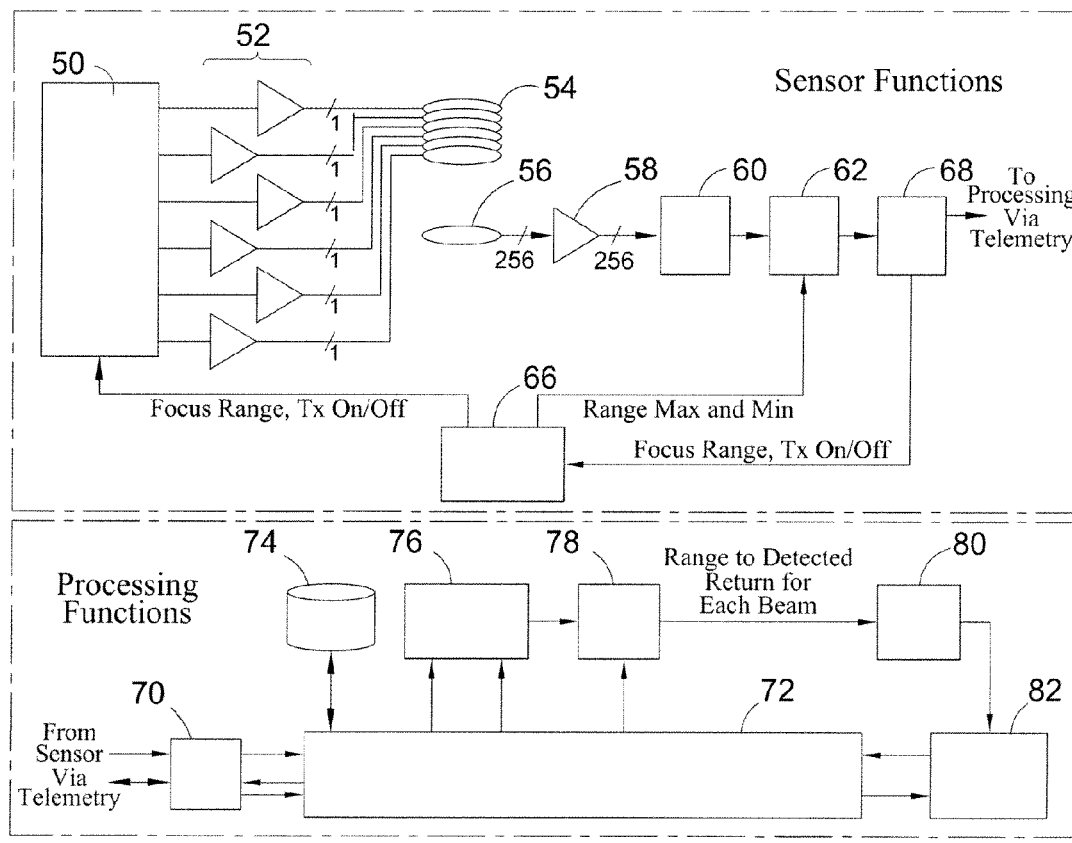
FIG. 9 is a functional block diagram of the system in accordance with an embodiment of the invention.

The combined effect from the steering and focussing of the transmit and receive beams is illustrated in FIG. 9. By focussing both transmit and the receive beams 18, 30 at the same distance from the cylindrical acoustic sensor it is possible to focus them onto a surface or boundary at a focus region 32, the focus region 32 being narrow in both orthogonal planes. Thus with the imaging sensor array nominally at the centre of a pipe, for example, high resolution images of the inside surface of the pipe can be created well inside the far field limit, by moving the sensor (probe) down the pipe.

Figure 10:
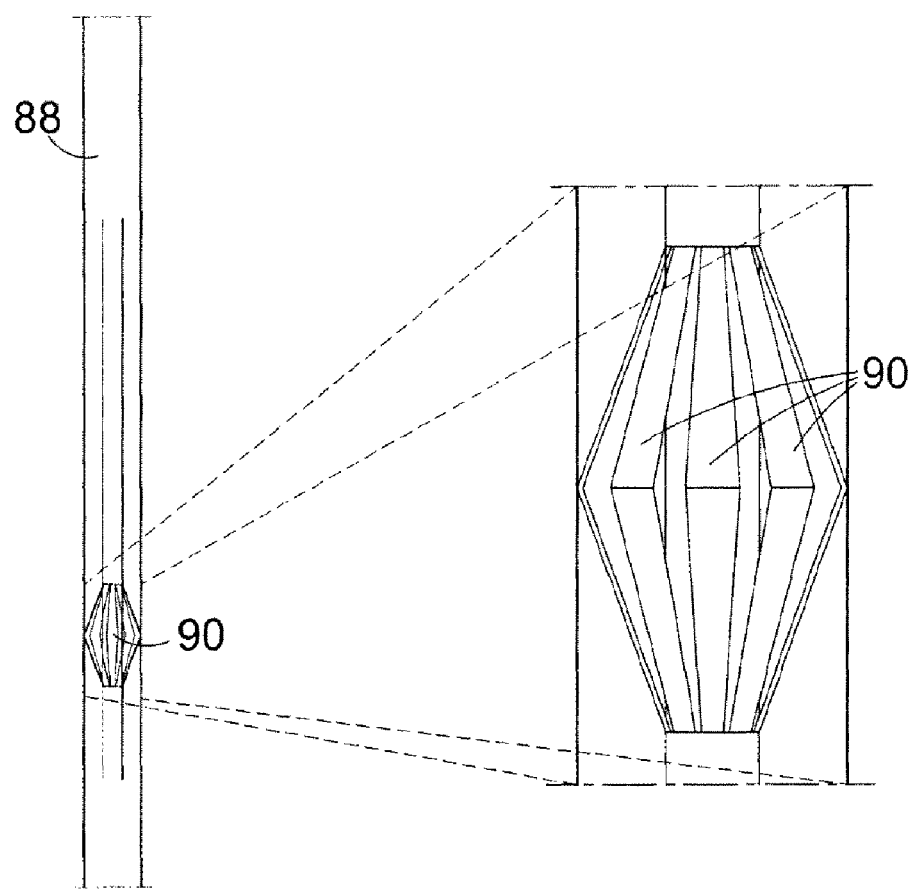
FIG. 10 illustrates an arrangement for locating a sensor array in a pipe according to an embodiment of the invention.

One of the applications of the probe 2 is for inspecting the inside surface of a pipe used in the extraction of oil on an oilrig. An important feature is to maintain concentricity between the probe and the pipe hence the cylindrical shape of the probe is the most convenient. The mechanism for passing the probe down along the pipe whilst maintaining it approximately concentric within the pipe is a spring arrangement, not shown, the same or similar to an existing spring mechanism used for holding a camera for passing down through the pipe. A suitable spring arrangement comprising a plurality of sprung arms 90 is shown in FIG. 10, the sprung arms 90 holding the sensor central to the pipe 88. The precision with which the probe 2 is concentrically aligned with the pipe is a function of the depth of field of focussing. It does not have to be exact.

In embodiments described above the array of acoustic transmitters are rings disposed around the circumference of the cylindrical probe 2. It is possible to have the transmitters not as complete rings but arranged in juxtaposed or spaced arcs on the probe surface, and the array of acoustic receivers 8 may be disposed likewise as an arc on the probe surface. Typically, the arcs may subtend 60, 90 or 180 degrees, enabling a full scan of an inner concentric surface to be established by relative angular rotation in steps of 60, 90 or 180 degrees between the probe 2 and concentric surface under inspection, such as the inside surface of a pipe.

Whereas the probe 2 has been described above as having a cylindrical body, it is possible for the body to be non-cylindrical, for example the acoustic transmitter array 4 and receiver array may be formed around the surface of a probe having a square or other polygonal cross-section. In such an embodiment the arrays may also be formed either completely around the circumferential surface or on just portions thereof, for example located on one or two of the side surfaces defining the polygonal shape.

In a further aspect of the invention there is provided a method of sonar imaging an area under investigation, comprising transmitting beams from a transmitter array, receiving reflected acoustic signals from the area under investigation, which are sensed by acoustic receiver sensors in a receiver array to produce a plurality of output signals from said acoustic receiver sensors, and processing said output signals to provide an image of the area under investigation, wherein the transmitter beams are focussed from the transmitter array onto portions of the area to be examined in a plane orthogonal to the plane used to focus the receive beams.

In a yet further aspect of the invention there is provided a sonar array configuration the configuration comprising a transmitter array for transmitting sonar signals to an area under investigation and a receiver array of sonar sensors for receiving reflected acoustic signals, said array of sonar transmitters being located relative to the sonar receivers in a disposition whereby transmitter beams can be focussed from the transmitter array onto portions of the area to be examined in a plane orthogonal to the plane used to focus the receive beams.

In a further aspect of the invention there is provided a probe comprising the sonar array configuration defined above.

In a further aspect of the invention there is provided a method of inspecting the inside surface of a pipe containing a fluid, the method comprising inserting into the pipe a probe carrying a sonar array configuration having a transmitter array and a receiver array, transmitting beams from the transmitter array through the fluid to an area of the surface to be imaged, receiving reflected acoustic signals from the area under investigation which are sensed by acoustic receiver sensors in a receiver array to produce a plurality of output signals from said acoustic receiver sensors, and processing said output signals to provide an image of the area under investigation, wherein the transmitter beams are focussed from the transmitter array onto portions of the area to be examined in a plane orthogonal to the plane used to focus the receive beams.

In one embodiment of the method the pipe is an oil extraction pipe and the fluid is oil.

FIG. 9 illustrates a system suitable for use in imaging the internal surface of a pipe. A PP (pipe profile) waveform generator 50 drives, by way of respective amplifiers 52, each of the rings of a PP projector array 54. A PP hydrophone receiver array 56 also shown for receiving reflected signals from the pipes surface. The receiver array consists of 256 hydrophones the output of each of which is fed via a respective pre-amplifier 58 to an analogue to digital converter 60.

The output from the ADC 60 is fed to one of the inputs of a range gate 62, which is adapted to pass only those signals received by it within a predetermined period T, starting a predetermined time $T_d$ after each transmission. The period T starting a time $T_d$ after transmission is calculated as being the time window when acoustic signals will be received from the pipe. If the signals are received earlier or later, i.e. outside the predetermined period T, it is assumed they were created by something other than a first reflection off the inside surface of the pipe. The maximum and minimum range is set by a sensor controller 66 connected to an input of the range gate 62 and to the waveform generator 50.

If for example, the pipe has an internal diameter of 10 cms, and the distance between the sensors and the internal pipe wall is estimated as approximately 3 cms, the range gate may be set to pass signals expected within the range 2 cm to 4 cm between the sensors and internal pipe wall, giving a 1 cm tolerance to take account of variations. This tolerance can of course be varied dependent on other applications of the system and other parameters of the system.

The signals falling within the period T are fed to an interface 68, incorporating a buffer, before being transmitted by telemetry to a system controller 72 via a processor interface 70. The controller 72, together with other components which define the processing functions, may be provided on the oil rig platform.

The system controller 72 is coupled to a data storage medium 74, a pipe profile beamformer 76, and a detector 78, the beamformer 76 also being connected to the detector. The range for the detected return of each beam is passed to a display processor 80 and then to a display 82. The image at the display 82 is typically created as a running image and colour coded to showing the variations in range detected between the receiver array and the pipe wall. In this way damage to the pipe can be detected.

The system controller 72 controls the focus range and the on/off function of the transmitter array by control signals passed via the interfaces 70, 68 to the sensor controller 66, the sensor controller 66 controlling the waveform generator 50 accordingly.

In order to detect a possible blockage in the pipe a sonar sensor can be attached to the end of the probe to detect any blockage as the probe moves along the pipe.

The invention claimed is:

1. An acoustic imaging system for imaging a structure, the system comprising:
   a probe having a plurality of arrays of acoustic transmitters, the acoustic transmitters of each array being arranged in a juxtaposed or spaced relationship around at least a portion of a circumferential surface of the probe, the acoustic transmitter arrays being in a juxtaposed or spaced relationship longitudinally on the probe;
   an array of acoustic receivers disposed radially around at least a portion of the circumferential surface of the probe; and
   a beam-former to focus and to steer a plurality of acoustic transmit beams from the array of acoustic transmitters onto at least a portion of the structure to be examined and to focus and to steer a plurality of receive beams from said structure, said beam-former adapted to cause the plurality of acoustic transmit beams to be focussed in a plane orthogonal to a plane used to focus the plurality of receive beams.

2. The acoustic imaging system as claimed in claim 1, further comprising a controller to focus automatically the plurality of receive beams, dependent on range and speed of sound, and to focus the plurality of transmit beams, by one of preset selection or real-time operator selection, on said portion of the structure to be examined.

3. The acoustic imaging system as claimed in claim 2, further comprising an apparatus to focus and to steer transmit and receive beams onto or from, respectively, a surface at a focus region, the focus region being narrow in two orthogonal planes.

4. The acoustic imaging system as claimed in claim 1, further comprising an apparatus to focus and to steer transmit and receive beams onto or from, respectively, a surface at a focus region, the focus region being narrow in two orthogonal planes.

5. The acoustic imaging system as claimed in claim 1, wherein the probe has a cylindrical configuration, the transmitter and the receiver arrays sharing a common central axis through the cylindrical configuration.

6. The acoustic imaging system as claimed in claim 5, wherein the transmit and receive arrays are adapted to scan an inside surface of a pipe, the system further comprising a mechanism to guide the probe along the inside of the pipe while keeping the arrays and the inside surface of the pipe in approximate concentric alignment to one another.

7. The acoustic imaging system as claimed in claim 1, wherein the transmitter arrays are formed as a plurality of juxtaposed or spaced rings extending around an outer surface of the probe, each ring comprising at least one transmitter element.

8. The acoustic imaging system as claimed in claim 1, wherein the receiver array comprises a single ring of receiver elements.

9. The acoustic imaging system as claimed in claim 1, wherein the arrays of acoustic transmitters are arranged in juxtaposed or spaced arcs on the circumferential surface of the probe.

10. The acoustic imaging system as claimed in claim 1, wherein the array of acoustic receivers is arranged as an arc on the circumferential surface of the probe.

11. The acoustic imaging system as claimed in claim 1, wherein the transmit and receive arrays are adapted to scan an inside surface of a pipe, the system further comprising a mechanism to guide the probe along the inside of the pipe while keeping the arrays and the inside surface of the pipe in approximate concentric alignment to one another.

12. The acoustic imaging system as claimed in claim 1 wherein the transmitter arrays are arranged to transmit acoustic beams that are omni-directional in a radial plane of the probe and narrow in an orthogonal plane of the probe.

13. The acoustic imaging system as claimed in claim 1, wherein the transmitter and receiver arrays are adapted to focus the transmit beams in a plane orthogonal to a plane used to focus the receive beams.

14. A method of sonar imaging an area to be examined, comprising the steps of:
   transmitting a plurality of transmitter beams from a plurality of arrays of acoustic transmitters, the acoustic transmitters of each array being arranged in a juxtaposed or spaced relationship around at least a portion of a circumferential surface of a probe, the arrays of acoustic transmitters being in a juxtaposed or spaced relationship longitudinally on the probe;
   receiving reflected beams from an area to be examined, the received beams sensed by an array of acoustic receivers disposed radially around at least a portion of the circumferential surface to produce a plurality of output signals from said array of acoustic receivers; and
   processing said plurality of output signals to provide an image of the area to be examined,
   wherein the plurality of transmitter beams are focussed and steered from the arrays of acoustic transmitters onto predetermined portions of the area to be examined in a plane orthogonal to the plane used to focus and steer the received beams.

15. The method as claimed in claim 14, further comprising the step of dynamically controlling the focal point of at least one of the arrays of acoustic transmitters and array of acoustic receivers.

16. The method as claimed in claim 14, further comprising the steps of:
   steering transmit and receive beams, respectively, onto or from a surface; and
   focussing transmit and receive beams, respectively, at a focus region, the focus region being narrow in two orthogonal planes.

17. The method as claimed in claim 16, further comprising the step of guiding the transmit and receive arrays along a pipe while keeping the arrays of acoustic transmitters, array of acoustic receivers, and the surface to be examined in approximately concentric alignment to one another, in order to scan the inside surface of the pipe.

18. The method as claimed in claim 14, further comprising the step of guiding the transmit and receive arrays along a pipe while keeping the arrays of acoustic transmitters, array of acoustic receivers, and the surface to be examined in approximately concentric alignment to one another, in order to scan the inside surface of the pipe.

* * * * *